United States Patent [19]

Kohn et al.

[11] Patent Number: 5,216,115

[45] Date of Patent: Jun. 1, 1993

[54] POLYARYLATE CONTAINING DERIVATIVES OF THE NATURAL AMINO ACID L-TYROSINE

[75] Inventors: Joachim B. Kohn, Highland Park, N.J.; James J. Fiordeliso, Rochester, N.Y.

[73] Assignee: Rutgers, The State University of New Jersey, New Brunswick, N.J.

[21] Appl. No.: 930,146

[22] Filed: Aug. 13, 1992

Related U.S. Application Data

[60] Continuation-in-part of Ser. No. 804,767, Dec. 9, 1991, which is a division of Ser. No. 536,425, Jun. 12, 1990, Pat. No. 5,009,060.

[51] Int. Cl.⁵ .................. C08G 63/00; C08G 63/06; C07C 229/00
[52] U.S. Cl. .................................. 528/176; 528/182; 528/206; 560/40
[58] Field of Search ............... 528/176, 219, 182, 206; 560/40

[56] References Cited

U.S. PATENT DOCUMENTS 3,586,713  6/1971  Buu-Hoi .......................... 564/170
4,579,866  4/1986  Stevenson et al. ................. 560/40

Primary Examiner—John Kight, III
Assistant Examiner—T. Mosley
Attorney, Agent, or Firm—Lerner, David, Littenberg, Krumholz & Mentlik

[57] ABSTRACT

Bioerodible polyarylates derived from biocompatible dicarboxylic acids and natural amino acid-derived diphenol starting materials. Molded articles and controlled drug delivery systems prepared from the polyarylates are also disclosed.

15 Claims, 2 Drawing Sheets

POLYARYLATE CONTAINING DERIVATIVES OF THE NATURAL AMINO ACID L-TYROSINE

CROSS-REFERENCE TO RELATED APPLICATIONS

This application is a continuation-in-part of U.S. patent application Ser. No. 804,767, filed Dec. 9, 1991, which application, in turn, is a divisional of U.S. patent application Ser. No. 536,425, filed on Jun. 12, 1990, which issued as U.S. Pat. No. 5,099,060 on Mar. 24, 1992. The disclosures of both applications are incorporated herein by reference thereto.

BACKGROUND OF THE INVENTION

The present invention relates to amino acid-derived bioerodible polymers and to methods of synthesizing such polymers. In particular, the present invention relates to bioerodible polyarylates derived from the natural amino acid L-tyrosine and biocompatible dicarboxylic acids.

Polyesters in general are highly useful and intensively studied materials. Polyesters have been classified according to the nature of the polyhydric compounds and dicarboxylic acids from which the polymers are derived. Polyesters derived from aromatic polyhydric compounds are classified as polyarylates, with polyarylates of aliphatic diacids classified as aliphatic polyarylates and polyarylates of aromatic diacids classified as aromatic polyarylates. Polyesters derived from aliphatic polyhydric compounds and aliphatic diacids are classified as aliphatic polyesters, and polyesters derived from aliphatic polyhydric compounds and aromatic diacids are classified as aliphatic-aromatic polyesters. See Imai et al., "Synthesis and Characterization of Aromatic Polyesters," *Handbook of Polymer Science and Technology*, Vol. 1, N. Cheremisinoff, ed., Marcel Dekker, Inc., New York and Basel, 1989), 177–208.

A wide range of aliphatic polyesters (e.g., poly(lactic acid), poly(glycolic acid), polydioxanone, poly(hydroxybutyrate), polycapro-lactone and the like) have been explored as biomaterials, especially in the context of degradable medical implants because of their hydrolytic instability. See, Huang, "Biodegradable Polymers," *Encyclopedia of Polymer Science and Technology*. (F. H. Mark et al., ed., John Wiley and Sons, New York 1985), vol. 2, 220–43. Because of their hydrolytic instability, however, aliphatic polyesters are not used as industrial engineering plastics.

Aliphatic-aromatic polyesters include poly(ethylene terephthalate) (PET) and poly(butylene terephthalate) (PBT). Some aliphatic-aromatic polyesters are very important commercial plastics, but (with the exception of DACRON ®) have not been widely investigated in the biomaterials area. DACRON ® is a PET used as an artificial vascular graft. See, Silver et al., *Biocompatibility: Interactions of Biological and Implantable Materials*, vol. 1, (VCH Publishers, New York, 1989) 240–3. Aliphatic-aromatic polyesters are hydrolytically much more stable than aliphatic polyesters and are degraded under physiological conditions at such a slow rate that they are regarded as "nondegradable."

Aromatic polyarylates have recently gained importance as liquid crystalline polymers. These polymers are derived from aromatic dicarboxylic acids and diphenols (bisphenols). Many aromatic polyarylates possess highly desirable properties for use as engineering plastics, such as formation of strong films and fibers which are heat, solvent and flammability resistant.

In addition, some aromatic polyarylates are electric insulators and exhibit liquid crystalline behavior. For example, Carborundum marketed poly(p-hydroxybenzoic acid) under the trade name of EKKONOL ® in 1970. Shortly thereafter, ICI, Tennessee Eastman, Celanese and DuPont marketed polyarylates derived from iso- and terephthalic acids and bisphenols such as hydroquinone, substituted hydroquinones and Bisphenol A. See, Gaudiana, "Polyesters, Main Chain Aromatic," *Encyclopedia of Polymer Science and Engineering*, (Mark et al., ed., John Wiley and Sons, New York, 1985) vol. 2, 264–6. The major disadvantage of these early polyarylates was that they were difficult to process because of their high melting points. More recently, new polyarylates that are more easily processable have been obtained through modification of the monomers, copolymerization and blending.

Aliphatic polyarylates are a fourth class of polyester and are derived from aromatic diols and aliphatic diacids. Examples of aliphatic polyarylates include poly(hydroquinone-adipate) and poly(Bisphenol A-sebacate). These polymers have less commercial appeal because they do not generally possess the high thermal stability of the aromatic polyarylates. The synthesis of aliphatic polyarylates from bisphenols and aliphatic dicarboxylic acids was first reported by British Patent Nos. 621,102 and 636,429. In the early work, hydroquinone and aliphatic dicarboxylic acids were used to develop aliphatic polyarylates of high melting points and hydrolytic stability. See, Eareckson, *J. Polym. Sci.*, 40, 399–406 (1959), Egorova et al., *Vysokomolekul. Soedin.*, 2. 1475 (1960) and Mikhailov et al., *Khim Volokna*, 1963(2), 19–22 (1963).

Particularly important are the studies of Morgan, *J. Polym. Sci., Part A*2, 437–59 (1964) who synthesized a series of aliphatic polyarylates using either phenolphthalein or Bisphenol A as the diphenol components. By varying the length of the diacid, Morgan established the first systematic structure-property correlations for this class of polymers. Morgan noted that all the polymers prepared were amorphous, soluble in a variety of organic solvents, and had relatively low softening temperatures. Thus, these materials were not the high temperature engineering plastics sought by industry. Many other aliphatic polyarylates were later synthesized, for example, from resorcinol, dihydroxynapthalenes, bis(4-hydroxyphenyl) alkanes and phthaleins. See, Morgan, *Condensation Polymers: By Interfacial and Solution Methods*, (Interscience Publishers, New York, 1965) 334–41.

Commonly owned U.S. Pat. No. 5,099,060 discloses amino acid-derived diphenol compounds, the chemical structures of which were designed to be particularly useful in the polymerization of polycarbonates and polyiminocarbonates. The resulting polymers are useful as degradable polymers in general, and as tissue compatible bioerodible materials for biomedical uses, in particular. The suitability of these polymers for this end-use application is the result of their derivation from naturally occurring amino acids. In particular, the polyiminocarbonates and polycarbonates are polymerized from L-tyrosine derived diphenols.

The L-tyrosine derived polyiminocarbonates are rapidly biodegradable, while their polycarbonate counterparts degrade very slowly. This patent suggests that when a material having a moderate degree of bioerodibility is required, that the two polymers be blended to achieve the required rate of biodegradation. While this adequately addresses this requirement, a need remains for biodegradable polymers having a moderate rate of hydrolytic degradation.

Aliphatic polyarylate type polyesters would be expected to have a moderate rate of biodegradation. Such compounds could be prepared from the L-tyrosine derived diphenols used in the preparation of the polycarbonates and polyiminocarbonates disclosed by U.S. Pat. No. 5,099,060. However, unlike the polycarbonates and polyiminocarbonates, which are polymerized by linking biocompatible amino acid-derived diphenols by way of non-amide linkages to provide a nontoxic polymer that forms nontoxic degradation products, the polymerization of polyesters requires the reaction of a diacid with the diphenol. Diacids are therefore also required that will produce a nontoxic polymer that forms nontoxic degradation products.

There is no disclosure in the prior art that tyrosine-derived diphenols specifically designed for the polymerization of mechanically strong polyiminocarbonates and polycarbonates would also form polyarylates with favorable engineering properties when reacted with various aliphatic and aromatic dicarboxylic acids. Furthermore, the synthesis of polyarylates using the amino acid-derived diphenols of U.S. Pat. No. 5,099,060 poses a challenge because of the relative inertness of these diphenols in polyesterifications and because of the presence of a chemically sensitive aliphatic ester bond in the monomer structure. Contrary to the formation of aliphatic polyesters in which the thermodynamic equilibrium favors esterification, the synthesis of polyarylates requires the activation of the diacid. Traditional methods of synthesis utilize diacid chloride derivatives as the active intermediates in either solution or interfacial polymerization reactions. Transesterifications at elevated temperatures and direct polycondensations using a variety of condensing agents have also been explored. See, Imai et al., "Synthesis and Characterization of Aromatic Polyesters," *Handbook of Polymer Science and Technology*.

Aliphatic polyarylates of intermediate molecular weight (inherent viscosity about 0.52) were prepared by Morgan, *J. Polym. Sci., Part A2*, 437–59 (1964) under mild conditions of low temperature and pressure, through the diacid chloride and direct polycondensation routes. In the diacid chloride interfacial reaction a strongly basic aqueous solution of the bisphenolate anion is reacted with a solution of a diacid chloride in a water-immiscible organic solvent such as dichloromethane. The reaction occurs at the interface and is accelerated by the use of a quaternary ammonium or phosphonium salt or by a phase transfer catalyst such as a crown ether. See, Conix, *Ind. Eno. Chem.*, 51, 147 (1959). The diacid chloride reaction can also be done in an organic solvent and a base such as triethylamine is often used to neutralize liberated hydrogen chloride. See, Morgan, *J. Polym. Sci., Part A2*, 437–59 (1964).

The direct polycondensation route has significant advantages over the diacid chloride technique in the laboratory preparation of aliphatic polyarylates. The need for the unstable diacid chlorides is eliminated, and the diphenol can have functional groups that would be incompatible with the reactive diacid chlorides or the strongly basic aqueous solutions required in the interfacial technique. Direct polycondensation thereby facilitates the use of base-sensitive diphenols as monomers, such as the amino acid-derived diphenols disclosed in U.S. Pat. No. 5,099,060.

A variety of condensing agents have been used in the polymerization of aliphatic polyarylates, including triphenylphosphine (see, Ogata et al., *Polym. J.*, 13(10), 989–91 (1981) and Yasuda et al., *J. Polym. Sci.: Polym. Chem. Ed.*, 21, 2609–16 (1983)), picryl chloride (see, Tanaka et al., *Polym. J.*, 14(8), 643–8 (1982)), phosphorus oxychloride with lithium chloride monohydrate as a catalyst (see, Higashi et al., *J. Polym. Sci.: Polym. Chem. Ed.*, 24, 589–94 (1986)), arylsulfonyl chlorides (see, Higashi et al., *J. Polym. Sci.: Poly. Chem. Ed.*, 21, 3233–9 (1983)), diphenyl chlorophosphate (see, Higashi et al., *J. Polym. Sci.: Polym. Chem. Ed.*, 21, 3241–7 (1983)), thionyl chloride with pyridine (see, Higashi, *J. Polym. Sci.: Polym. Chem. Ed.*, 24, 97–102 (1986)), triethylamine as a base (see Elias et al., *Makromol. Chem.*, 182, 681–6 (1981)) and diisopropylcarbodiimide with the specially designed catalyst 4-(dimethylamino) pyridinium 4-toluenesulfonate (DPTS) (see, Moore et al., *Macromol.*, 23(1), 65–70 (1990)). Although numerous aliphatic polyarylates have thus been prepared, they have usually been derived from bioincompatible diacid or bisphenol components and would therefore not be expected to be suitable as degradable medical implant materials.

There remains a need for nontoxic polyarylates having a moderate rate of bioerosion, suitable for use as tissue-compatible materials for biomedical uses.

SUMMARY OF THE INVENTION

It has now been discovered that amino acid-derived diphenols can be copolymerized with dicarboxylic acids by way of a carbodiimide-mediated direct polycondensation to form nontoxic bioerodible polyarylates having numerous biomedical uses. In addition to being nontoxic in polymeric form, the polyarylates of the present invention are expected to form nontoxic degradation products. Furthermore, the polyarylates of the present invention degrade by hydrolytic chain cleavage under physiological conditions, which makes it possible to use the polymers as degradable, medical implant materials.

Therefore, according to one aspect of the present invention, aliphatic and aromatic polyarylates are provided that have repeating structural units according to Formula I:

wherein X is selected from —H, —NHL$_1$, —NL$_1$L$_2$,

Y is hydrogen or a pendant group having the structure:

wherein L$_1$, L$_2$ and L$_3$ are independently selected from straight or branched alkyl and alkylaryl groups having up to 18 carbon atoms; and R is selected from saturated and unsaturated, substituted and unsubstituted alkyl, aryl and alkylaryl groups containing up to 18 carbon atoms.

The polyarylates of the present invention meet the need for a moldable biodegradable biocompatible polymer derived from nontoxic monomeric starting materials. The polymer is expected to hydrolyze to release the original diphenol and diacid, thus forming nontoxic degradation products, provided the monomeric starting materials are nontoxic. The toxicological concerns associated with polyarylates are met by using diphenols derived from L-tyrosine dipeptides and dicarboxylic acids that are either important metabolites or highly biocompatible compounds. Therefore, another aspect of the present invention provides molded articles prepared from the polyarylates of the present invention.

The polyarylates of the present invention include polymers having pendant side chains on each repeating unit. This structural feature represents a further degree of freedom in the design of polyarylates and can be used to modify the overall physicomechanical properties of the polymer without changing the polymer backbone structure. Detailed studies correlating the structure of pendant chains with the physicomechanical properties of polyarylates have apparently never been performed.

In addition, a biologically or pharmacologically active agent can be chemically incorporated into the pendant X and Y side chains of the polymer. Alternatively, the pendent side chains can be used to crosslink the polymer chains to form a polymeric matrix into which a biologically or pharmacologically active material can be physically imbedded or dispersed.

Therefore, another aspect of the present invention includes polyarylates having repeating structural units according to Formula I in which R is the same as described with respect to Formula I and $L_1$, $L_2$ or $L_3$ of X and Y include pharmacologically or biologically active ligands. Still yet another aspect of the present invention provides polyarylates having repeating structural units according to Formula I in which X, Y and R are the same as described with respect to Formula I, wherein the polyarylate is physically admixed with a biologically or pharmacologically active material.

Another aspect of the present invention provides amino acid-derived monomers that are capable of being polymerized to form polyarylates. The monomers provided by this aspect of the present invention are diphenol compounds that are tyrosine derivatives having the structure of Formula II:

(II)

in which X and Y are the same as described above with respect to Formula I. Among the monomers of Formula II are the desaminotyrosyl-tyrosine esters of parent U.S. Pat. No. 5,099,060 used in the preparation of polycarbonates and polyiminocarbonates in which X is hydrogen and Y is:

wherein $L_3$ is an alkyl group containing up to 18 carbon atoms.

This aspect of the present invention incorporates the discovery that useful polyarylates can be prepared from tyrosine-derived diphenol compounds with the N-terminus present and suitably protected, as well as C-terminus protecting groups.

A further aspect of the present invention provides an improved carbodiimide-mediated direct polyesterification process for the polymerization of polyarylates using 4-(dimethylamino)pyridinium-p-toluene sulfonate (DPTS) as a catalyst. A polymerization process according to this aspect of the invention includes the steps of contacting a diphenol with a dicarboxylic acid in a common solvent for the diphenol and the dicarboxylic acid in the presence of a catalytic amount of DPTS and an excess of carbodiimide, and recovering the resulting polyarylate.

This aspect of the present invention represents a modification of the procedure of Moore et al., to use an excess of the carbodiimide coupling reagent. This modification unexpectedly increases the molecular weight of the polymers obtained to over 50,000 daltons. It is noteworthy that this modification to increase the amount of coupling reagent is contrary to the conventional wisdom employed when selecting the amount of coupling reagent to be used to mediate direct polyesterifications.

The understanding of the ordinarily skilled artisan is that the molar equivalents of the coupling reagent utilized should not exceed the molar equivalents of the functional groups to be coupled. Thus, Moore et al. used a ratio of from 1.3 to 2.0 equivalents of coupling reagent to 2.0 equivalents of functional groups to be coupled. By going against such conventional wisdom, the inventive process significantly increases the molecular weights obtained for the polyarylates to levels heretofore unknown in the art.

DETAILED DESCRIPTION OF THE PREFERRED EMBODIMENTS

The polyarylates of the present invention employ diphenol compounds derived from dimers of L-tyrosine as a starting material. L-tyrosine derived diphenol compounds suitable for the polymerization of polyarylates have the structure depicted by Formula II in which X and Y are the same as described above with respect to Formula I.

L-tyrosine is a naturally occurring amino acid. Among the preferred L-tyrosine derivatives of Formula II are derivatives in which X is hydrogen. These preferred compounds are tyrosine dipeptide analogs known as desaminotyrosyl-tyrosine. Desaminotyrosine (Dat) itself occurs naturally in plants. In this preferred group, the diphenol can be regarded as a pseudodipeptide.

The preferred desamino-tyrosyl-tyrosine compounds of Formula II are those compounds in which Y is:

wherein $L_3$ is an alkyl or alkylaryl group containing up to 18 carbon atoms. In this particularly preferred group, the diphenol starting material is properly referred to as a desaminotyrosyl-tyrosine alkyl or alkylaryl ester. The preferred monomers of the group of desaminotyrosyl-tyrosine esters are the ethyl, butyl, hexyl, octyl and benzyl esters. The most preferred ester is the hexyl ester, referred to as desaminotyrosyl-tyrosine hexyl ester, or DTH.

The preparation of the diphenol starting materials can be depicted by the following scheme:

C-terminus protected alkyl and alkylaryl esters of tyrosine containing up to 8 carbon atoms are prepared according to the procedure disclosed in J. P. Greenstein and M. Winitz, *Chemistry of the Amino Acids*, (John Wiley & Sons, New York 1961), p. 929. C-terminus protected alkyl and alkylaryl esters of tyrosine containing more than 8 carbon atoms are prepared according to the procedure disclosed in Overell, U.S. Pat. No. 4,428,932.

N-terminus protected tyrosines are prepared following standard procedures of peptide chemistry such as disclosed in Bodanszky, *Practice of Peotide Synthesis* (Springer-Verlag, New York, 1984). The protection of either terminus is omitted if X or Y of Formula II is hydrogen.

The crude tyrosine derivatives are sometimes obtained as oils and can be purified by simple recrystallization. Crystallization of the pure product is accelerated by crystal seeding.

The diphenols are then prepared by carbodiimide mediated coupling reactions in the presence of hydroxybenzotriazide following standard procedures of peptide chemistry such as disclosed in Bodanszky, *Practice of Peptide Synthesis* (Springer-Verlag, New York, 1984) at page 145. The crude diphenols can be recrystallized twice, first from 50% acetic acid and water and then from a 20:20:1 ratio of ethyl acetate, hexane and methanol, or, alternatively, flash chromatography on silica gel is used, employing a 100:2 mixture of methylene chloride:methanol as the mobile phase. DTH is prepared by the carbodiimide mediated coupling of desaminotyrosine and tyrosine hexyl ester in the presence of hydroxybenzotriazole.

The diphenol compounds are then reacted with aliphatic or aromatic dicarboxylic acids in a carbodiimide-mediated direct polyesterification using DPTS as a catalyst to form aliphatic or aromatic polyarylates. Dicarboxylic acids suitable for the polymerization of polyarylates have the structure of Formula III:

in which, for the aliphatic polyarylates, R is selected from saturated and unsaturated, substituted and unsubstituted alkyl or alkylaryl groups containing up to 18 carbon atoms, and preferably from 2 to 12 carbon atoms. For the aromatic polyarylates, R is selected from aryl groups containing up to 18 carbon atoms and preferably from 6 to 12 carbon atoms.

R is preferably selected so that the dicarboxylic acids employed as starting materials are either important naturally-occurring metabolites or highly biocompatible compounds. Preferred aliphatic dicarboxylic acid starting materials therefore include the intermediate dicarboxylic acids of the cellular respiration pathway known as the Krebs Cycle. These dicarboxylic acids include alpha-ketoglutaric acid, succinic acid, fumaric acid, malic acid and oxaloacetic acid, for which R is $-CH_2-CH_2-C(=O)-$, $-CH_2-CH_2-$, $-CH=CH-$, $-CH_2-CH(-OH)-$ and $-CH_2-C(=O)-$, respectively.

Another naturally-occurring, preferred, aliphatic dicarboxylic acid starting material is adipic acid ($R=(-CH_2-)_4$), found in beet juice. Still yet another preferred biocompatible aliphatic dicarboxylic acid is sebacic acid ($R=(-CH_2-)_8$), which has been studied extensively and has been found to be nontoxic as part of the clinical evaluation of poly(bis(p-carboxyphenoxy) propane-co-sebacic acid anhydride) by Laurencin et al., *J. Biomed. Mater. Res.*, 24, 1463-81 (1990). Other preferred biocompatible aliphatic dicarboxylic acids include oxalic acid (no R), malonic acid ($R=(-CH_2-)$), glutaric acid ($R=(-CH_2-)_3$), pimelic acid ($R=(-CH_2-)_5$), suberic acid ($R=(-CH_2-)_6$) and azelaic acid ($R=(-CH_2-)_7$). In other words, among the aliphatic dicarboxylic acids suitable for use in the present invention are compounds in which R represents $(-CH_2-)Z$, wherein Z is an integer between zero and 12, inclusive.

Among the preferred aromatic dicarboxylic acids suitable for use in the present invention are terephthalic acid, isophthalic acid and bis(p-carboxyphenoxy) alkanes such as bis(p-carboxyphenoxy) propane. The biocompatibility of bis(p-carboxyphenoxy) propane is disclosed by the above-cited Laurencin et al., *J. Biomed. Mater. Res.*

Because the diphenols of the present invention are base-sensitive, the polyarylates of the present invention are prepared by direct polyesterification, rather than by diacid chloride techniques. Polyesterification condensing agents and reaction conditions should be chosen that are compatible with the base-sensitive diphenol starting materials. Thus, the polyarylates can be prepared by the process disclosed by Ogata et al., *Polym. J.*, 13(10), 989-91 (1981) and Yasuda et al., *J. Polym. Sci.: Polym. Chem. Ed.*, 21, 2609-16 (1983) using triphenylphosphine as the condensing agent, the process of Tanaka et al., *Polym. J.*, 14(8), 643-8 (1982) using picryl chloride as the condensing agent, or by the process of Higashi et al., *J. Polym. Sci.: Polym. Chem. Ed.*, 24, 589-94 (1986) using phosphorus oxychloride as the condensing agent with lithium chloride monohydrate as a catalyst.

The polyarylates can also be prepared by the method disclosed by Higashi et al., *J. Polym. Sci.: Polym. Chem. Ed.*, 21, 3233-9 (1983) using arylsulfonyl chloride as the condensing agent, by the process of Higashi et al., *J. Polym. Sci.: Polym. Chem. Ed.*, 21, 3241-7 (1983) using diphenyl chlorophosphate as the condensing agent, by the process of Higashi et al., *J. Polym. Sci.: Polym. Chem. Ed.*, 24, 97-102 (1986) using thionyl chloride with pyridine as the condensing agent, or by the process of Elias, et al., *Makromol. Chem.*, 182, 681-6 (1981) using thionyl chloride with triethylamine. A preferred polyesterification procedure is the method disclosed by Moore et al., *Macromol.*, 23, 65-70 (1990) utilizing carbodiimide coupling reagents as the condensing agents with the specially designed catalyst DPTS.

A particularly preferred polyesterification technique modifies the method of Moore to utilize an excess of the carbodiimide coupling reagent. This produces aliphatic polyarylates having molecular weights greater than those obtained by Moore. Essentially any carbodiimide commonly used as a coupling reagent in peptide chemistry can be used as a condensing agent in the preferred polyesterification process. Such carbodiimides are well-known and disclosed in Bodanszky, *Practice of Peptide Synthesis* (Springer-Verlag, New York, 1984) and include dicyclohexylcarbodiimide, diisopropylcarbodiimide, 1-(3-dimethylaminopropyl)-3-ethyl carbodiimide hydrochloride, N-cyclohexyl-N'-(2'-morpholinoethyl)-carbodiimide-metho-p-toluene sulfonate, N-benzyl-N'-3'- dimethylaminopropyl-carbodiimide hydrochloride, 1-ethyl-3-(3-dimethylaminopropyl)carbodiimide methiodide, N-ethylcarbodiimide hydrochloride, and the like. The preferred carbodiimides are dicyclohexyl carbodiimide and diisopropylcarbodiimide.

A reaction mixture is formed by contacting exactly equimolar quantities of the diphenol and the dicarboxylic acid in a solvent for the diphenol and the dicarboxylic acid. Suitable solvents include methylene chloride, tetrahydrofuran, dimethylformamide, chloroform, carbon tetrachloride and N-methyl pyrrolidinone. It is not necessary to bring all reagents into complete solution prior to initiating the polyesterification reaction, although the polymerization of slightly soluble monomers such as desaminotyrosyltyrosine ethyl ester and succinic acid will yield higher molecular weight polymers when the amount of solvent is increased. The reaction mixture can also be heated gently to aid in the partial dissolution of the reactants.

In this particularly preferred method, the reaction mixture will also contain an excess of the carbodiimide coupling reagent. When carbodiimides are used in peptide synthesis as disclosed by Bodanszky, between 0.5 to 1.0 molar equivalents of carbodiimide reagent is used for each mole of carboxylic acid group present. In the present invention, greater than 1.0 molar equivalents of carbodiimide per mole of carboxylic acid group present are used. This is what is meant by describing the reaction mixture as containing an excess of carbodiiide.

The polymer molecular weight significantly increases as the amount of coupling reagent used is increased. The degree of molecular weight increase only begins to level off around four molar equivalents of carbodiimide per mole of carboxylic acid group. Increasing the amount of coupling reagent beyond four equivalents of carbodiimide has no further beneficial effect. While quantities of carbodiimide greater than four equivalents are not detrimental to the polyesterification reaction, such quantities are not cost-effective and are thus not favored for this reason.

The carbodiimide-mediated direct polyesterification is performed in the presence of the catalyst DPTS. DPTS is prepared in accordance with the procedure of Moore et al., *Macromol.*, 23(1), 65-70 (1990). The amount of DPTS is not critical because the material is a true catalyst that is regenerated. The catalytically effective quantity is generally between about 0.1 and about 2.0 molar equivalents per mole of carboxylic acid group, and preferably about 0.5 equivalents per mole of carboxylic acid group.

The reaction proceeds at room temperature, or about 20-30° C. The reaction mixture can be heated slightly (<60° C.) prior to carbodiimide addition to partially solubilize less soluble monomers. However, the polymerization reaction itself should be conducted between 20° C. and 30° C. Within this temperature range, the reaction can be continued, with stirring, for at least 12 hours, and preferably for from one to four days. The polymer is recovered by quenching the reaction mixture in methanol, from which the polyarylate usually precipitates while the residual reagents remain in solution. The precipitate may be separated by mechanical separations such as filtration and purified by solvent washing.

In a preferred procedure, equimolar amounts of pure, dried tyrosine-derived diphenol and dicarboxylic acid are weighed precisely ($\pm 0.0001$ g) and placed in a round-bottomed flask, pre-dried at 130°0 C. A suitable magnetic stir bar is placed into the flask. Then 0.4 equivalents of DPTS are added. The flask is fitted with a septum and flushed with nitrogen or argon to remove traces of moisture from the reaction mixture. Next, a quantity of HPLC grade methylene chloride is added via a syringe and the reaction mixture is stirred vigorously to suspend the reactants. The amount of methylene chloride used will depend upon the solubility of the diphenol, or the dicarboxylic acid, or both monomers. At this stage, the reaction mixture may be slightly heated to partially dissolve the monomers. While it is not essential that the monomers be completely dissolved, the quantity of solvent should be sufficient to dissolve the polymer as it forms and thus slowly bring the monomers into solution.

4.0 equivalents of diisopropylcarbodiimide are then added to the reaction mixture via a syringe. After about 10 minutes, the reaction mixture becomes clear, followed by the formation of a cloudy precipitate of diiospropylurea. After stirring between 20° C. and 30° C. for one to four days, the reaction is terminated by pouring the reaction mixture slowly and with vigorous stirring into ten volumes of methanol. The polymer precipitates while the residual reagents remain dissolved in methanol, resulting in the formation of the clear supernatant.

The polymeric product is retrieved by filtration and washed with copius amounts of methanol to remove any impurities. If desired, the polymeric products can be further purified by dissolving in methylene chloride (10% or 20% w/w) and reprecipitating in methanol. The polymeric product is then dried to constant weight under high vacuum.

The polyarylates of the present invention thus include one or more recurring structural units represented by Formula I as described above, with X, Y and R being the same as described above with respect to Formula I. The recurring structural units of preferred polyarylates are represented by Formula I as described above, with X being hydrogen and Y being:

with $L_3$ being an alkyl or alkylaryl group containing up to 18 carbon atoms and preferably being an ethyl, butyl, hexyl, octyl or benzyl group. R is a saturated or unsaturated, substituted or unsubstituted, alkyl, aryl or alkylaryl group containing up to 18 carbon atoms and is preferably a saturated or unsaturated, substituted or unsubstituted alkyl group containing from 2 to 12 carbon atoms.

Preferred polyarylates have weight-average molecular weights above 50,000 daltons, and preferably above 100,000 daltons. Molecular weights are calculated from gel permeation chromatography relative to polystyrene standards without further correction.

The polyarylates can be worked up by known methods commonly employed in the field of synthetic polymers to produce a variety of useful articles with valuable physical and chemical properties, all derived from tissue compatible monomers. The useful articles can be shaped by conventional polymer-forming techniques such as extrusion, compression molding, injection molding, and the like. Molded articles prepared from the polyarylates are useful, inter alia, as degradable biomaterials for medical implant applications. Such applications include the use of the molded articles as vascular grafts and stents, bone plates, sutures, implantable sensors, barriers for surgical adhesion prevention, implantable drug delivery devices and other therapeutic aids and articles which decompose harmlessly within a known period of time.

The polyarylates can also be formed into drug delivery implants that degrade to release pharmacologically or biologically active agents within a predictable controlled release time. Such controlled drug delivery systems can be prepared by incorporating the active agents into the polymer chains as pendant side chains or by cross linking the pendant side chains to form a polymeric matrix into which the active agents are physically embedded or dispersed. Controlled drug delivery system implants can also be formed by physically admixing the polyarylates with a biologically or pharmacologically active agent. The foregoing procedures are essentially conventional and well-known to those of ordinary skill in the art.

Biologically or pharmacologically active agents can be chemically incorporated into pendant side chains of polyarylates having repeating structural units according to Formula I, wherein X is an unprotected amino group (N-terminus) or Y is an unprotected carboxylic acid group (C-terminus). The formation of polyarylates having de-protected N- or C-termini from the polyarylates of the present invention having protected N- or C-termini can be achieved by the use of temporary protecting groups as disclosed by Bodanszky. The selective use of such temporary protecting groups is well-known to those of ordinary skill in the art of peptide synthesis.

A variety of pharmacologically or biologically active ligands having functional groups capable of being coupled to a free amino or carboxylic acid group can then be covalently incorporated into the deprotected monomeric units of the polyarylates by conventional coupling techniques. The resulting polyarylate has repeating structural units according to Formula I in which X is $-NHL_1$, $-NL_1L_2$:

or Y is:

wherein $L_1$, $L_2$ or $L_3$ is a pharmacologically or biologically active ligand.

$L_1$ or $L_2$ of X include pharmacologically or biologically active ligands which have a free carbocylic acid group through which the ligand is covalently bonded to X. Such ligands are selected from ibuprofen, methotrexate, N-acetyl-cis-hydroxyproline, cephadrine, ampicillin, and the like. $L_3$ of Y includes pharmacologically or biologically active ligands which have a free amino or hydroxyl group, through which the ligand is covalently bonded to Y. Such ligands are selected from dopamine, cis-hydroxyproline ethyl ester, doxorubicin, histamine, ampicillin, cephradine, and the like.

For controlled drug delivery systems in which a biologically or pharmacologically active agent is physically embedded or dispersed into a polymeric matrix or physically admixed with a polyarylate, suitable biologically or pharmacologically active agents include in principle any active agent that has to be repeatedly administered over prolonged periods of time.

The following non-limiting examples set forth hereinbelow illustrate certain aspects of the invention. All parts and percentages are by weight unless otherwise noted and all temperatures are in degrees Celsius. Dicarboxylic acids and all other reagents were purchased in pure form and were used as received. Solvents were of "HPLC grade." All diphenolic monomers (e.g., the ethyl, butyl, hexyl and octyl esters of desaminotyrosyltyrosine) were prepared according to the procedure provided in Example I of U.S. Pat. No. 5,099,060. Although this procedure refers specifically to DTH, monomers having esters other than the hexyl ester (including the benzyl ester) can be readily prepared by the same basic procedure. The DPTS catalyst was prepared as described by Moore et al., *Macromol.*, 23(1), 65–70 (1990).

EXAMPLES

The examples use the following polymer characterization procedures.

Spectroscopy

RT-IR spectra were recorded on a Matson Cygnus 100 spectrometer. Polymer samples were dissolved in methylene chloride and films were cast directly onto NaCl plates. All spectra were collected after 60 scans at 4 cm$^{-1}$ resolution. UV-visible spectra were recorded on a Perkin-Elmer lambda 3B spectrophotometer. NMR spectra were recorded on a Varian VXR-200 spectrometer.

Molecular Weights

Molecular weights were determined by gel permeation chromatography (GPC) on a chromatographic system consisting of a Perkin-Elmer Model 410 pump, a Waters Model 410 RI detector, and a PE-Nelson Model 2600 computerized data station. For polymer analysis, 2 PL-gel GPC columns (300 nm×7.7 nm, particle size 5 micron, pore size $10^5$ and $10^3$ Angstrom, respectively) were placed in series and were operated at a flow rate of 1 mL/min in DMF containing 0.1% (w/v) of LiBr or in methylene chloride. Molecular weights were calculated relative to polystyrene standards without further corrections.

Thermal Properties

The glass transition temperature ($T_g$) was measured with a DuPont 910 Differential Scanning Calorimeter (DSC) calibrated with idium. The decomposition temperature ($T_d$) was measured with a DuPont 951 Thermogravimetric Analyzer at a heating rate of 10° C./min.

Solvent Casting

The polymer (1.5 g) was dissolved in 25 mL of methylene chloride. The solution was filtered through a syringe filter (0.45 micron pore, 25 mm PTFE filter) and poured into a 4"×4" glass mold in a glove bag under nitrogen. The film was first dried for three days in the glove bag, followed by drying in high vacuum to constant weight.

Mechanical Properties

The mechanical properties of thin, solvent-cast polymer films were measured on an Instron Tensile Tester according to ASTM standard D882-83. In all cases, unoriented, non-crystalline films were used, yielding results that were representative of the bulk properties of the polymers at room temperature.

Hydrolytic Degradation Studies

Samples of various shapes and sizes were cut from solvent cast films. The samples were incubated at 37° C. in phosphate buffer-saline solution (0.1M, pH 7.4) containing 200 mg/L sodium azide to inhibit bacterial growth. The degradation process was followed weekly by recording the weight change of five individual samples, by measuring the residual polymer molecular weight, by solution and by surface analysis (FTIR, ESCA and SEM) and by mechanical property testing of partly degraded samples after exposure to the buffer solution.

Model "Drug Release" Studies

An exactly weighed amount of p-nitroaniline (pNA) was dissolved in methylene chloride. To this solution, an exactly weighed amount of polymer was added, such that the required ratio of dye to polymer was obtained. Any undissolved residues were removed by filtration through a 0.45 micron membrane filter. The filtered solutions were then used for solvent casting as described above. Homogeneous and transparent films were obtained. Release devices (circular disks, diameter approximately 1.0 cm, thickness about 0.01–0.03 cm, weight about 10–40 mg) were excised from the dried films with a cork borer.

The release devices were placed into 10 mL of phosphate buffer (0.1 M, pH 7.4) and kept at 37° C. The amount of dye released was determined spectrophotometrically. After each such analysis, the device was transferred into fresh, sterile phosphate buffer.

The following table defines the abbreviations adopted for the diphenols and polyarylates illustrated by the examples below:

TABLE I

| | |
|---|---|
| Desaminotyrosyl-tyrosine hexyl ester | DTH |
| Desaminotyrosyl-tyrosine ethyl ester | DTE |
| Desaminotyrosyl-tyrosine octyl ester | DTO |
| Poly(DTH succinate) | DTH-suc |
| Poly(DTH adipate) | DTH-AA |
| Poly(DTH sebacate) | DTH-SA |
| Poly(DTE adipate) | DTE-AA |
| Poly(DTO adipate) | DTO-AA |
| Poly(DTH terephthalate) | DTH-Tere |

EXAMPLE 1

DTH-suc was prepared by placing DTH (10.3380 g, 0.025 moles) and succinic acid (2.9523 g, 0.025 moles), into a 500 mL dry flask. DPTS (2.9940 g, 0.4 equivalents) was added and after sealing the flask and flushing with nitrogen, methylene chloride (180 mL) was added. The reaction mixture was stirred vigorously to suspend the reactants.

Diisopropylcarbodiimide (12.6230 g 4.0 equivalents) was added via syringe. After four (4) day, the reaction was terminated by pouring the reaction mixture into 1,800 mL of methanol. The crude polymer was purified by dissolving in methylene chloride (20% w/w) and reprecipitating from 110 mL of methanol.

8.18 g of a colorless polymer was obtained (66% of theoretical yield) having a weight average molecular weight of 102,000 daltons, a number average molecular weight of 68,000 daltons and a polydispersity of 1.50.

EXAMPLE 2

DTH-AA was prepared by placing DTH (8.2712 g, 0.020 moles) and adipic acid (2.9228 g, 0.020 moles) into a 500 mL dry flask. DPTS (2.3552 g, 0.4 equivalents) was added and after sealing the flask and flushing with nitrogen, methylene chloride (150 mL) was added. The reaction mixture was stirred vigorously to suspend the reactants. Diisopropylcarbodiimide (10.0984 g, 4.0 equivalents) was added via syringe. After one day, the reaction was terminated by pouring the reaction mixture into 1,500 mL of methanol. The crude polymer was purified by dissolving in methylene chloride (5% w/w) and reprecipitating from 500 mL of methanol.

5.58 g of a colorless polymer was obtained (53% of theoretical yield). The polymer had a weight average molecular weight of 232,000 daltons, a number average molecular weight of 132,000 daltons and a polydispersity of 1.76.

EXAMPLE 3

DTH-SA was prepared by reacting sebacic acid (5.0560 g, 0.025 moles) with 0.025 moles of DTH according to the procedure described in Example 1. Following purification by dissolving in methylene chloride and reprecipitating from methanol, 11.32 g of a colorless polymer was obtained (76% of theoretical yield). The polymer had a weight average molecular weight of 212,000 daltons, a number average molecular weight of 133,000 daltons and a polydispersity of 1.59.

EXAMPLE 4

DTE-AA was prepared by placing DTE (8.9100 g, 0.025 moles) and adipic acid (3.6535 g, 0.025 moles) in a 500 mL dry flask. DPTS (2.9440 g, 0.4 equivalents) was added and after sealing the flask and flushing with nitrogen, methylene chloride (275 mL) was added. The reaction mixture was stirred vigorously to suspend the reactants. Diisopropylcarbodiimide (12.6230 g, 4.0 equivalents) was added Via syringe. After one day, the reaction was terminated by pouring the reaction mixture into 1,800 mL of methanol. The crude polymer was purified by dissolving in methylene chloride (20% w/w) and reprecipitation from 80 mL of methanol.

7.66 g of a colorless polymer was obtained (66% of theoretical yield). The polymer had a weight average molecular weight of 151,000 daltons, a number average molecular weight of 68,000 daltons and a polydispersity of 2.2.

EXAMPLE 5

DTO-AA was prepared by placing DTO (9.7148 g, 0.022 moles) and adipic acid (3.2151 g, 0.022 moles) into a 300 mL dry flask. DPTS (2.5907 g, 0.4 equivalent) was added and after sealing the flask and flushing with nitrogen, methylene chloride (140 mL) was added. The reaction mixture was stirred vigorously to suspend the reactants. Diisopropylcarbodiimide (11.1082 g, 4.0 equivalents) was added via syringe. After one day, the reaction was terminated by pouring the reaction mixture into 1,400 mL of methanol. The crude polymer was purified by dissolving in methylene chloride (20% w/w) and reprecipitation from 100 mL of methanol.

9.52 g of a colorless polymer was obtained (78% of theoretical yield). The polymer had a weight average molecular weight of 218,000, a number average molecular weight of 128,000 and a polydispersity of 1.70.

Thermal Properties

Several batches of polymers were prepared according to the examples given above. The thermal properties of these polymers were analyzed as described above and are listed in Table II. The aliphatic polyarylates listed here have glass transition temperatures between 17° C. and 56° C. and become soft enough for compression and injection molding about 40° C. above their respective glass transitions. Because the decomposition temperatures are well above 300° C. in all cases, the polymers can be readily processed by thermal polymer processing techniques.

TABLE II

| Polymer Name | $M_w$ (daltons) | $M_n$ (daltons) | $T_g$ (°C.) | $T_d$ (°C.) |
|---|---|---|---|---|
| DTH-suc | 102,000 | 68,000 | 45 | 371 |
| DTH-AA | 232,000 | 132,000 | 34 | 356 |
| | 208,000 | 85,000 | 33 | 360 |
| | 186,000 | 126,000 | 32 | 356 |
| DTH-SA | 212,000 | 133,000 | 17 | 368 |
| DTE-AA | 209,000 | 114,000 | 56 | 340 |
| DTO-AA | 218,000 | 128,000 | 28 | 357 |

Degradation Studies

A degradation study was started for the adipic acid series (DTE-AA, DTH-AA and DTO-AA) to determine the time frame and mechanism for degradation. During the first five weeks of the study, none of the polymers lost any weight. However, a decrease in molecular weight was detected, confirming the degradability of the polymers under physiological conditions. The decrease in molecular weight is shown in FIG. 1.

The rate of degradation will most probably be controlled by the overall hydrophobicity of the polymer and its morphological state. In terms of overall hydrophobicity, the rate of degradation should decrease with increasing length of the polymer side chain. In terms of morphological state, polymers that are in the rubbery state at 37° C. should degrade faster than polymers that are in the glassy state at that temperature. Thus, the glass transition temperature ($T_g$) becomes the second rate determining parameter in the degradation process.

Figure 1:
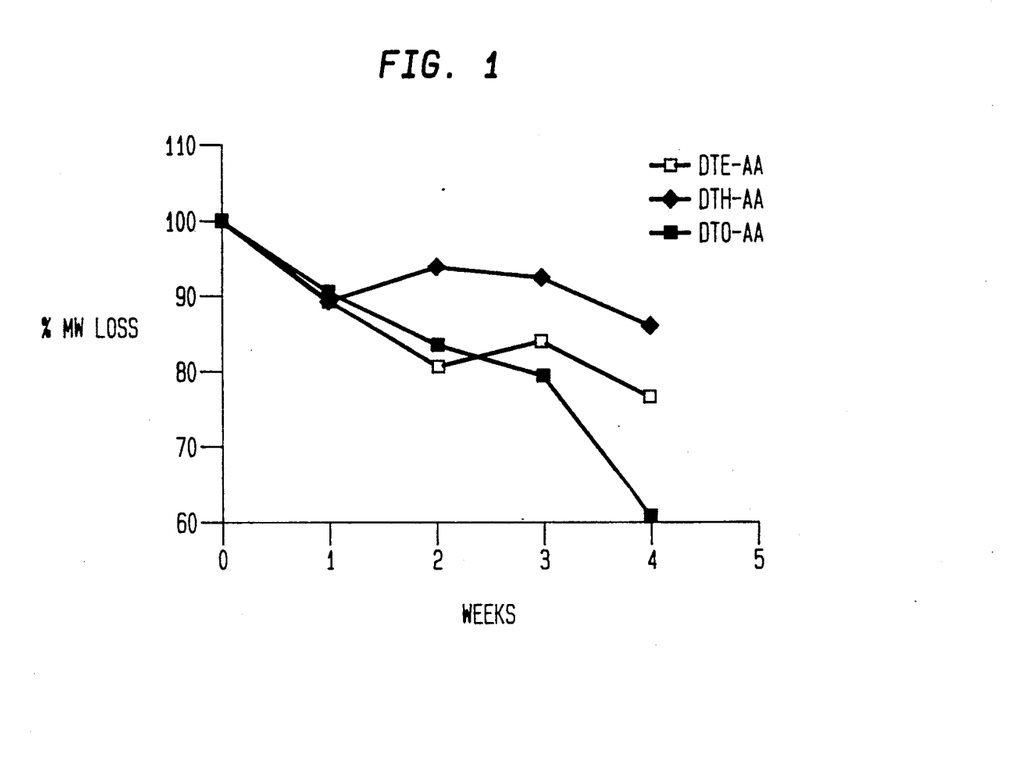
FIG. 1 depicts the molecular weight degradation for adipic acid-derived aliphatic polyarylate embodiments of the present invention.

As shown in FIG. 1, from the data obtained over the initial five weeks, DTO-AA appears to degrade fastest. This polymer is indeed in the rubbery state at 37° C., while the polymers that appear to degrade the least, DTE-AA and DTH-AA, have higher glass transition temperatures. Thus, the current invention indicates that there are at least two interrelated parameters (length of side chain and glass transition temperature) that can be used to control the rate of degradation of tyrosine-derived polyarylates.

Model Drug Release Studies

Figure 2:
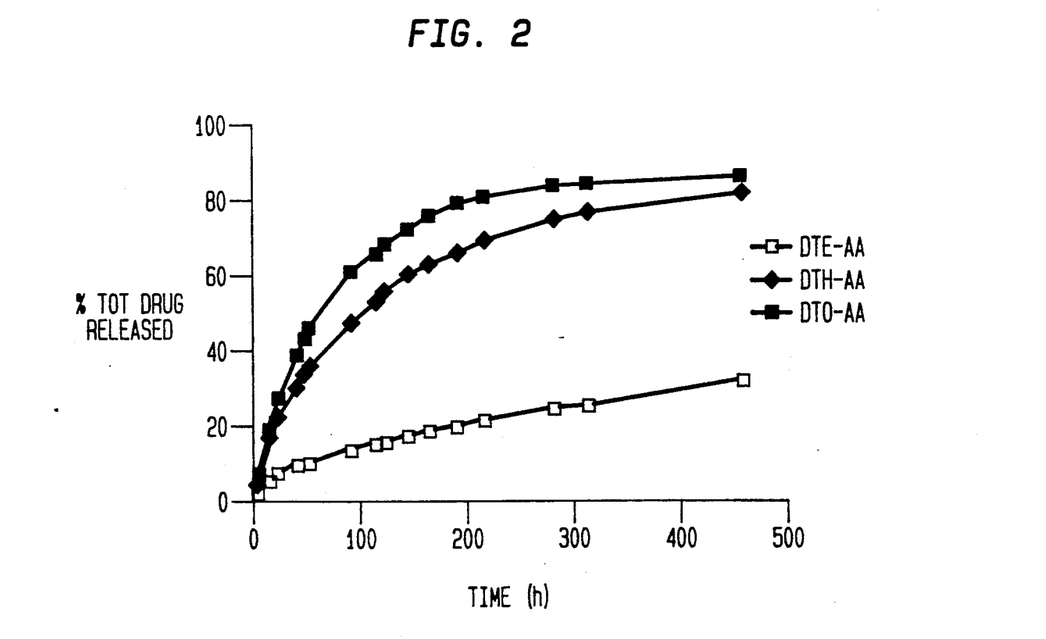
FIG. 2 depicts a model drug release profile for the aliphatic polyarylates of FIG. 1 using p-nitroaniline as the agent released.
Figure 3:
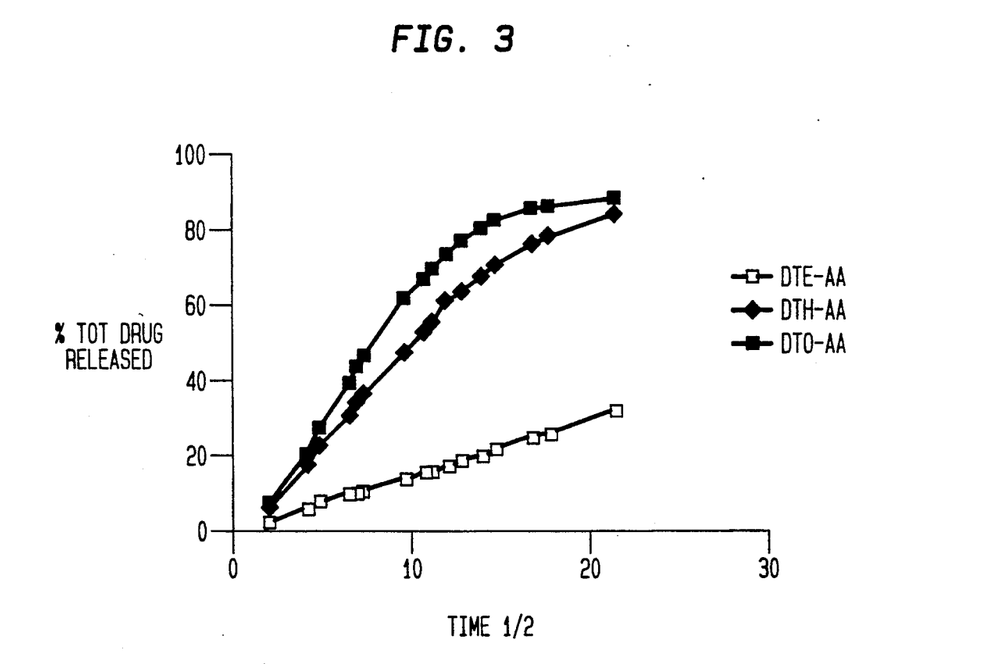
FIG. 3 depicts the model drug release profile of FIG. 2 as a function of the square-root of time.

Preliminary model drug release studies were performed for the polymers in the adipic acid series in an attempt to establish the feasibility of using tyrosine-derived polyarylates as implantable drug release formulations. In these studies, p-nitroaniline (pNA) served as a model "drug" because its release can be conveniently monitored by UV-visible spectroscopy. The release profiles of pNA from disk-shaped polymer devices loaded with 5% (w/w) of pNA are shown in FIGS. 2 and 3.

It is evident that the release rate is related to the morphological state of the polymer, with polymers in the rubbery state releasing much faster than polymers in the glassy state. Thus, the order of drug release increases with increasing side chain length (ethyl to hexyl to octyl) corresponding to the decrease in the polymer glass transition temperature. This is illustrated in Table III, which correlates the release rate (slope of the FIG. 3 release curves) with the glass transition temperatures of the respective polymers.

TABLE III

| Polymer Name | Slope (sec$^{-1}$) | $T_g$ (°C.) |
|---|---|---|
| DTE-AA | 2.98 × 10$^{-4}$ | 56 |
| DTH-AA | 8.56 × 10$^{-4}$ | 33 |
| DTO-AA | 11.21 × 10$^{-4}$ | 28 |

The difference between FIG. 2 and FIG. 3 is in the representation of the data. FIG. 2 shows the accumulated fraction of drug released as a function of time, while FIG. 3 shows the accumulated fraction of drug released as a function of the square root of time. The fact that a significant portion of the release profiles in FIG. 3 are straight lines is an indication that drug release in the systems is predominantly "diffusion controlled." The release rates (as defined by the slopes of the linear regions of the release profiles in FIG. 3) are related to the $T_g$ of the polymer, indicating that it will be possible to formulate a wide range of drug delivery systems by selecting different polymers from among the tyrosine-derived polyarylates.

Obviously, drugs other than pNA will have release characteristics different from the data shown in FIGS. 2 and 3. The data shown here simply intend to demonstrate the potential usefulness of aliphatic polyarylates in the area of drug delivery.

PHYSICOMECHANICAL PROPERTIES

Preliminary mechanical property studies have been done for the polymers DTH-AA, DTH-SA, DTE-AA and DTO-AA and the results are tabulated in Table IV:

TABLE IV

| Polymer Name | Tensile Strength (MPa) | % Elongation at break |
|---|---|---|
| DTE-AA | 37.1 | 7 |
| DTH-AA | 37.2 | 498 |
| DTO-AA | 44.2 | 634 |
| DTH-SA | 46.4 | 727 |

Basically, each polymer differs in appearance, ductility and viscoelasticity depending upon whether the polymer is in the glassy state or the rubbery state at room temperature. Because DTE-AA is in the glassy state at room temperature, it is much less ductile than the other three polymers. All polymers in the series can be oriented by heating above $T_g$ and stretching. Oriented films are significantly stronger than unoriented films. DTH-SA is the most ductile of the four polymers. It can be stretched to long extensions and will return back to its original shape. This polymer thus shows elastomeric behavior at room temperature.

EXAMPLE 6

DTH-Tere was prepared by reacting terephthalic acid (1.1629 g, 0.007 moles) with 0.007 moles of DTH (2.8949 g) in a 250 mL dry flask according to the procedure described in Example 1. Unlike the reactions involving aliphatic acids, the reaction mixture never cleared up, reflecting the decreased solubility of the reagents. Instead, a gelatinous polymeric mass formed. After one day, the reaction was terminated by pouring the reaction mixture into 800 mL of methanol. The resulting product was dried under high vacuum overnight.

3.54 g of a colorless polymer was obtained (93% of theoretical yield). Because of the insolubility of the polymeric product in common organic solvents, the molecular weight could not be determined.

THERMAL PROPERTIES OF DTH-Tere

Analysis of the polymer by DSC indicated that DTH-Tere has a glass transition at 96° C. and an additional endothermal transition at 190° C. The additional transition at 190° C. may be indicative of polymer crystallinity. The exact nature of this transition is currently not understood.

SOLUBILITY OF DTH-Tere IN ORGANIC SOLVENTS 10 mg aliquots of polymer were placed into test tubes and 2 mL of the indicated solvent were added. If the solution became clear, the polymer was classified as soluble. If the polymer appeared to swell or dissolve partially, it was classified as partially soluble. If no change occurred, the polymer was classified as insoluble. Solvents in which the polymer was classified as partially soluble or insoluble were then heated to their respective boiling points and the polymer was observed again. The solubility of the polymer in various solvents with and without the application of heat is illustrated in Table V:

TABLE V

| Solvent | No Heat | Heat Applied |
|---|---|---|
| Dichloromethane | Insoluble | Insoluble |
| Chloroform | Partially Soluble | Partially Soluble |
| Tetrachloroethylene | Partially Soluble | Soluble |
| DMF/lithium bromide | Partially Soluble | Partially Soluble |
| Tetrahydrofuran | Insoluble | Insoluble |
| Pyridine | Partially Soluble | Soluble |
| Acetonitrile | Insoluble | Insoluble |
| Ethyl acetate | Insoluble | Insoluble |
| Ethyl ether | Insoluble | Insoluble |
| N-methyl pyrrolidinone | Partially Soluble | Soluble |

Accordingly, a family of polymers is provided having pendent chains and a backbone structure that can be readily varied to modify the thermal and physicomechanical properties. By modifying the polymer structure and thermal properties, the hydrolytic stability and the drug release properties of the polymers can be controlled.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. An amino acid-derived polyarylate comprised of one or more recurring structural units represented by the formula:

wherein X is selected from the group consisting of —H, —NHL$_1$, —NL$_1$L$_2$,:

Y is hydrogen or an ester group having the structure:

wherein $L_1$, $L_2$ and $L_3$ are independently selected from the group consisting of straight or branched alkyl and alkylaryl groups containing up to 18 carbon atoms and a biologically or pharmacologically active ligand; and

R is selected from the group consisting of saturated and unsaturated, substituted and unsubstituted alkyl, aryl and alkylaryl groups containing up to 18 carbon atoms.

2. The polyarylate of claim 1, which consists essentially of a single recurring structural unit repeating within said polymer.

3. The polyarylate of claim 1, having a weight-average molecular weight above 50,000 daltons, measured by gel permeation chromatography relative to polystyrene standards.

4. The polyarylate of claim 1, wherein X is hydrogen and Y comprises said ester group, wherein $L_3$ is selected from the group consisting of ethyl, butyl, hexyl, octyl and benzyl groups.

5. The polyarylate of claim 1, wherein X is selected from the group consisting of $-NHL_1$, $-NL_1L_2$,;

and either $L_1$ or $L_2$ comprises a pharmacologically or biologically active ligand covalently bonded within X via a free carboxylic acid group.

6. The polyarylate of claim 5, wherein said ligand is selected from the group consisting of ibuprofen, methotrexate, N-acetyl-cis-hydroxyproline, cephradine and ampicillin.

7. The polyarylate of claim 1, wherein Y comprises said ester group, and $L_1$ comprises a pharmacologically or biologically active ligand covalently bonded within Y via a free hydroxyl or amine group.

8. The polyarylate of claim 7, wherein said ligand is selected from the group consisting of dopamine, cis-hydroxyproline ethyl ester, cephradine, doxorubicin, histamine and ampicillin.

9. The polyarylate of claim 1, wherein R is selected from the group consisting of saturated and unsaturated, substituted and unsubstituted alkyl and alkylaryl groups containing from two to eight carbon atoms.

10. The polyarylate of claim 9, wherein R is selected from the group consisting of $-CH_2-C(=O)-$, $-CH_2-CH_2-C(=O)-$, $-CH=CH-$, $-CH_2-CH(-OH)-$ and $(-CH_2-)Z$, wherein Z is an integer between two and eight, inclusive.

11. The polyarylate of claim 1, wherein R is selected from the group consisting of substituted and unsubstituted aryl groups containing from 6 to 12 carbon atoms.

12. The polyarylate of claim 11, wherein said dicarboxylic acid is selected from the group consisting of phthalic acid, isophthalic acid and bis(p-carboxyphenoxy)alkanes.

13. A molded article prepared from the polyarylate of claim 1.

14. A controlled drug delivery system comprising the polyarylate of claim 1 physically admixed with a biologically or pharmacologically active agent.

15. A controlled drug delivery system comprising a biologically or pharmacologically active agent physically embedded or dispersed into a polymeric matrix formed from the polyarylate of claim 1.

* * * * *

UNITED STATES PATENT AND TRADEMARK OFFICE
CERTIFICATE OF CORRECTION

PATENT NO. : 5,216,115
DATED : June 1, 1993
INVENTOR(S) : Kohn et al.

It is certified that error appears in the above-identified patent and that said Letters Patent is hereby corrected as shown below:

On the title page, under the heading "Related U.S. Application Data" "[60]", "Pat. No. 5,009,060" should read --Pat. No. 5,099,060--.

Column 3, line 55, "Conix, Inc. Eno. Chem." should read --Conix, Ind. Eng. Chem.--.

Column 7, line 42, "Practice of Peotide Synthesis" should read --Practice of Peptide Synthesis--.

Column 9, line 58, "excess of carbodiiide" should read --excess of carbodiimide--.

Column 10, line 30, "130°0 C." should read --130°C.--.

Column 12, line 60, "lambda" should read --Lambda--.

Column 13, line 13, "calibrated with idium" should read --calibrated with indium--.

UNITED STATES PATENT AND TRADEMARK OFFICE
CERTIFICATE OF CORRECTION

PATENT NO. : 5,216,115
DATED : June 1, 1993
INVENTOR(S) : Kohn et al.

It is certified that error appears in the above-identified patent and that said Letters Patent is hereby corrected as shown below:

Column 18, lines 40-54, "the formula:

should read --the formula:

Signed and Sealed this

Eighth Day of March, 1994

*Attest:*

BRUCE LEHMAN

*Attesting Officer*     *Commissioner of Patents and Trademarks*